United States Patent
Kim et al.

(10) Patent No.: US 9,352,018 B2
(45) Date of Patent: May 31, 2016

(54) METHODS FOR TREATING NEUROLOGICAL DISEASES COMPRISING OSMOTIN

(75) Inventors: Myeong Ok Kim, Jinju-si (KR); M.L Narsimhan, Jinju-si (KR); M.L Naseer, Jinju-si (KR); R.A Bressan, Jinju-si (KR); Dae Jin Yun, Sacheon-Si (KR); Hae Young Lee, Jinju-Si (KR)

(73) Assignee: Industry-Academic Cooperation Foundation Gyeongsang National University, Jinju-si (KR)

( * ) Notice: Subject to any disclaimer, the term of this patent is extended or adjusted under 35 U.S.C. 154(b) by 61 days.

(21) Appl. No.: 13/811,893

(22) PCT Filed: Dec. 24, 2010

(86) PCT No.: PCT/KR2010/009317
§ 371 (c)(1),
(2), (4) Date: Apr. 4, 2013

(87) PCT Pub. No.: WO2011/090270
PCT Pub. Date: Jul. 28, 2011

(65) Prior Publication Data
US 2013/0210738 A1      Aug. 15, 2013

(30) Foreign Application Priority Data
Jan. 19, 2010   (KR) .................. 10-2010-0004940

(51) Int. Cl.
*A61K 38/16*   (2006.01)
*A23L 1/305*   (2006.01)

(52) U.S. Cl.
CPC ............. *A61K 38/168* (2013.01); *A23L 1/3055* (2013.01); *A23V 2002/00* (2013.01); *A61L 2430/32* (2013.01)

(58) Field of Classification Search
CPC ......................... A61K 38/168; A61L 2430/32
See application file for complete search history.

(56) References Cited

PUBLICATIONS

Jackowski, British Journal of Neurosurgery 9 (1995): 303-317.*
Liu et al., "Osmotin overespression in potato delays development of disease symptoms", Proc. Natl. Acad. Sci. USA, Plant Biology, vol. 91, pp. 1888-1892 (1994).
Kelesidis et al., "Adiponectin and cancer: a systematic review", British Journal of Cancer, vol. 94, No. 9, pp. 1221-1225 (2006).
Jung et al., "Adiponectin protects human neuroblastoma SH-SY5Y cells against acetaldehyde-induced cytotoxicity", Biochemical Pharmacology, vol. 72, pp. 616-623 (2006).
Sun et al., "Adiponectin, an Unlocking Adipocytokine", Cardiovascular Therapeutics, vol. 27, pp. 59-75 (2009).

* cited by examiner

*Primary Examiner* — Robert C Hayes
(74) *Attorney, Agent, or Firm* — Bret E. Field; Bozicevic, Field & Francis LLP

(57) ABSTRACT

The present invention relates to a composition for preventing and treating neurological diseases, and more particularly to a composition for preventing and treating neurological diseases comprising osmotin, a health functional food composition for preventing and ameliorating neurological diseases comprising osmotin, and a method of preventing or treating neurological diseases by administering the composition.

5 Claims, 15 Drawing Sheets

METHODS FOR TREATING NEUROLOGICAL DISEASES COMPRISING OSMOTIN

TECHNICAL FIELD

The present invention relates to a composition for preventing and treating neurological diseases, and more particularly to a composition for preventing and treating neurological diseases comprising osmotin, a health functional food composition for preventing and ameliorating neurological diseases comprising osmotin, and a method of preventing or treating neurological diseases by administering the composition.

BACKGROUND ART

The alcohol intake of human and animal mothers affects the brain development of the offspring. One basic mechanism is that ethanol reduces the number of neurons in various brain regions, such as cerebral cortices, hippocampi, cerebella and olfactory muscles. The reaction of ethanol leads to altered neuronal migration and increased cell death. Exposure to ethanol during brain development can provoke neurodevelopmental defects referred to as fetal alcohol effects (FAE) or fetal alcohol syndrome (FAS), depending on their severity, with an array of neurological disorders including hyperactivity, learning and memory deficits, mental retardation, psychosis, depression, and schizophrenia.

Ethanol causes craniofacial anomaly by apoptosis and neurodegeneration within 12 hours after exposure. Such neurodegeneration occurs because ethanol has NMDA antagonist and GABA mimetic properties and is responsible for the abnormal inhibition of neuronal activity, such as apoptosis induction.

Fetal alcohol spectrum disorders (FASD) appear in one of 100 children in USA, and it is known that many mechanisms, including oxidative stress, induction of apoptosis, excitotoxicity, destruction of cell-cell interaction, and inhibition of growth factor activity, contribute to neurotoxicity. Ethanol damages the developing brain by affecting neurogenesis, neuronal migration, or cell survival. This shows that FAS is the major non-genetic cause of mental retardation. Despite this increase in awareness of FAS, alcohol intake and excessive drinking during pregnancy have increased in recent years, and currently there are no effective treatments to prevent or revert FAS in the fetus in the mother.

The injury of free radicals and the rapid change in intracellular $Ca^{2+}$ are estimated to be elements of signaling pathways activated by ethanol exposure. During the brain growth spurt period in which the brain develops into a multicellular organism, neurons are sensitive to alcohol exposure. The human growth spurt spans the last trimester of pregnancy to several years after birth, but the rodent growth spurt occurs after birth. Thus, studies on alcohol exposure in developed animal models such as rodents are excellent means for investigating the mechanism about the effect of ethanol on human brain development.

Meanwhile, plant-derived osmotin is involved in regulation of fatty acid oxidation, glucose uptake, phosphorylation (AMP kinase) and signal transduction pathways. It is known that osmotin (24 kDa) is a stable protein belonging to the PR-5 family having homology with sweet-tasting protein thaumatin and induces intracellular signaling in yeasts. Osmotin is resistant to heat, acidity and enzymes, and can circulate through the body without being broken down by digestion. Such osmotin is homologous to adiponectin present in animals, and adiponectin appears to have anti-inflammatory, anti-diabetic and anti-atherogenic activities. However, osmotin has been studied mainly on its effects on obesity or diabetes, and other effects are not found.

Under these circumstances, the present inventors have made extensive efforts to investigate the effects of osmotin on neurodegenerative diseases and other neurological diseases, and as a result, have found that osmotin has the effect of inhibiting the induction of neuronal apoptosis to prevent and treat fetal alcohol effects (FAE) or fetal alcohol syndrome (FAS), which are accompanied by neurological disorders, learning and memory deficits, mental retardation, psychosis, depression, and schizophrenia, thereby completing the present invention.

DETAILED DESCRIPTION OF THE INVENTION

Technical Problem

It is an object of the present invention to provide a composition for preventing and treating neurological diseases comprising osmotin.

Another object of the present invention is to provide a health functional food composition for preventing and ameliorating neurological diseases comprising osmotin.

Still another object of the present invention is to provide a method for preventing or treating neurological diseases, the method comprising a step of administering a composition comprising osmotin to a non-human animal.

Technical Solution

In one aspect, the present invention is directed to a composition for preventing and treating neurological diseases comprising osmotin.

As used herein, the term "osmotin" refers to a protein that is abundantly contained in ripe fruits such as grapes and was first found 30 years ago. It was reported that osmotin functions similarly to proteins that inhibit obesity and diabetes in the human body, and it is known that osmotin can be used as a composition for treatment of some cancers. However, it has not been known that osmotin can function as a neuron-related protective substance.

The present inventors have first found that osmotin is capable of preventing or treating neuronal injury, and have also found that the above-described composition can be effective in protecting neuronal cells in a fetus in an early stage of development. In addition, the present inventors have demonstrated through specific experiments that, when the mother of a fetus in an early stage of development is exposed to a toxic substance such as alcohol to cause abnormalities in normal neuronal development, the neurons of the fetus can be protected by administering the above composition.

Moreover, with respect to the neuron protective effect of osmotin, the present inventors have found that, when neurons undergo apoptosis by an external substance or toxicity to affect normal neuronal development, osmotin exhibits the effect of protecting neurons by inhibiting apoptosis.

Osmotin is a protein that generally consists of about 150-250 amino acids and may consist of less than 150 or more than 250 amino acids depending on the kind of plant. Osmotin is known to be contained in the ripe fruits of plants, for example, *Nicotiana tabacum, Citrus sinensis, Rosa roxburghii, Solanum tuberosum, Piper colubrinum, Solanum tuberosum, Ricinus communis, Arabidopsis thaliana* and the like, but the kind of osmotin that is used in the present invention is not limited to the above examples. The origin of osmotin that is used in the present invention is not limited, and osmotin that is used in the present invention may be derived from various plants as described above or may be synthesized by genetic engineering methods known in the art.

The present inventors treated the brain neurons of rats at gestational day 17.5 (GD 17.5), and the brain neurons of rats at postnatal day 7 (P7) with osmotin, ethanol, or different concentrations of osmotin plus ethanol in order to examine the apoptosis of the neurons. As a result, it was seen that, in the group administered with osmotin, cytochrome-c release, caspase-3 activity and intracellular $Ca^{2+}$ were inhibited, the Bax/Bcl-2 ratio was reduced, and the mitochondrial membrane potential was restored, suggesting that apoptosis was inhibited.

For rats, osmotin of the present invention may preferably be administered at a dose of 0.001-1000 ug/g, more preferably 0.1-500 ug/g, even more preferably 0.2-10 ug/g, and most preferably 0.5-2 ug/g. If osmotin is administered at a dose of less than 0.001 ug/g, the effect on the prevention and treatment of neurological diseases will be insignificant, and if it is administered at a dose of more than 1000 ug/g, a further increase in the effect on the prevention and treatment of neurological diseases will not be obtained. However, the dose of osmotin can be experimentally determined by a person skilled in the art depending on various factors, including the kind, volume, characteristic and weight of cell or subject to be administered with osmotin.

Preferably, the composition of the present invention can be used without limitation for the prevention and treatment of neurological diseases in which neurons are involved. Examples of neurological diseases to which the composition of the present invention can be applied include, but are not limited to, Alzheimer's disease, Parkinson's disease, epilepsy, schizophrenia, depression, manic depression, neurodevelopmental disorder, autism, Lou Gehrig's disease, Huntington's disease, stroke, cerebral palsy, traumatic brain injury, dementia, progressive muscular atrophy, amyotrophic lateral sclerosis, post-polio syndrome, tabes dorsalis, multiple sclerosis, arm peripheral nerve disease, leg peripheral nerve disease, facial nerve palsy, Guillian-Barre's syndrome, Friedreich's ataxia, Charcot-Marie-Tooth disease, spina bifida, hydrocephalus, Down's syndrome, and chorea.

Preferably, neurological diseases which can be treated by the composition of the present invention include Alzheimer's disease, Parkinson's disease, HIV dementia, epilepsy, schizophrenia, depression, manic depression, neurodevelopmental disorder, autism, stroke, Lou Gehrig's disease, Huntington's disease, and multiple sclerosis. More preferably, the composition of the present invention can be used to prevent or treat fetal alcohol syndrome (FAS) caused by abnormalities in neuronal development in the neuronal development stage.

As used herein, the term "fetal alcohol syndrome (FAS)" refers to a group of physical and mental birth defects resulting from a women drinking alcohol heavily during pregnancy. Alcohol readily passes through the placenta, because the molecule thereof small. Thus, when the mother is exposed to alcohol, the alcohol level of the fetus is equal to that of the mother. Particularly, when the mother drinks alcohol in addition to smoking in a bad nutritional state or a severe stress state, the development rate of FAS further increases. In addition, it was reported that drinking alcohol in the early and late stages of pregnancy more severely affects the fetus, suggesting that not only alcohol intake, but also the timing of alcohol exposure greatly influence the fetus.

A child undergoing FAS generally shows four characteristic syndromes, including mental retardation, microcephaly, low weight and short palpebral fissure. In the facial appearance, there is no philtrum below the nose, the upper lip is significantly thinner than the lower lip, and the middle of the forehead is short while the eyes are small. Further, the child shows growth retardation, abnormalities in arms, legs and joints, learning disorder, heart disease, external genitalia and earlobe malformations. In addition, the child lacks the ability to move finely or greatly, has weak muscular strength while, showing tremors, behaves excessively or has poor sociality, and shows behavioral disorder such as loss of judgment. The above-described neurological diseases can be inhibited by administering the composition of the present invention to a mother at the early or late stage of pregnancy and the fetus at the stage of neuronal development.

As used herein, the term "prevention" refers to all actions that inhibit or delay neurological diseases by administering the composition.

As used herein, the term "treatment" refers to all actions that restore or beneficially change neurological diseases by administering the composition.

As used herein, the term "apoptosis" refers to cell death that is genetically programmed and is distinguished from cell death caused by tissue injury or pathogenic attack. Apoptosis plays a role in making the shape of the body in the developmental process and plays a role in protecting normal cells or removing abnormal cells in adults. It differs from programmed cell death (PCD) with respect to the loss of cells in cancer cells, viral infection and drugs, radiation, etc.

Preferably, the inventive composition comprising osmotin can prevent neuronal injury by inhibiting the apoptosis of neurons. Recently, the present inventors confirmed the effect of osmotin on the prevention or treatment of neurological diseases by analyzing the expression patterns of Bcl-2, Bax and cytochrome-c, which are known to be involved in apoptosis.

As used herein, the term "Bcl-2" refers to an apoptosis inhibitor, a member of the Bcl-2 family, which has a molecular weight of 26 kDa. It is known that Bcl-2 blocks apoptosis mediated by Fas antigen and TNF receptor, and thus the overexpression of Bcl-2 inhibits apoptosis to extend the cell life. Bcl-2 functions to inhibit Bax activity and the release of cytochrome C. On the other hand, "Bax" is known as an apoptosis inducer and belongs to the Bcl-2 because it has a nucleotide sequence similar to Bcl-2. The activation of Bax stimulates apoptosis to increase cell death, but the activation of Bcl-2 inhibits apoptosis to reduce cell death. Thus, the expression of Bcl-2 and Bax determine sensitivity when cells progress to apoptosis.

Preferably, the composition of the present invention can inhibit the apoptosis of neurons by reducing the Bax/Bcl-2 ratio.

Preferably, the composition of the present invention may further comprise pharmaceutically acceptable additives.

The additives may include carriers, excipients or diluents.

The composition of the present invention can be prepared as an oral or parenteral formulation according to the judgment of a person skilled in the art. Formulations can be prepared using diluents or excipients, such as fillers, extenders, binders, wetting agents, disintegrants and surfactants, which are commonly used.

The composition of the present invention can be prepared into oral formulations, such as powders, granules, tablets, pills, capsules, suspensions, extracts, emulsions, syrups and aerosols. Solid formulations for oral administration include tablets, pills, powders, granules, and capsules, and such solid formulations can be prepared by admixing at least one compound with at least one excipient, for example, starch, calcium carbonate, sucrose, lactose or gelatin etc. In addition to simple excipients, lubricants such as magnesium stearate or talc may also be used. Liquid formulations for oral administration include suspensions, solutions, emulsions, and syrup, and may contain various excipients, for example, wetting agents, flavoring agents, aromatics and preservatives, in addition to water and liquid paraffin, which are frequently used simple diluents. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like can be used. As the base of the suppositories, witepsol, Macrogol, Tween 61, cacao butter, laurin fat, glycerogelatin and the like can be used.

In another aspect, the present invention is directed to a health functional food composition for preventing or ameliorating neurological diseases comprising osmotin. Specifically, the composition of the present invention can be used simultaneously with or separately from a drug for treatment of diseases before or after the development of neurological diseases in order to prevent or ameliorate neurological diseases.

As used herein, the term "amelioration" refers to all actions that reduce a parameter related to the condition to be treated, for example, the degree of symptom.

If the health functional food composition of the present invention is used as a food additive, the composition can be added alone, or can be used in conjunction with other foods or food ingredients, or may be used appropriately according to conventional methods. Mixed amounts of active ingredients may be suitably determined depending upon the purpose of use (prophylactic, health or therapeutic treatment). Generally, when a food or a beverage is prepared, the composition of the present invention is added in an amount of 15 wt % or less and preferably 10 wt % or less, based on the total weight of the food or beverage. However, when prolonged intake is intended for the purpose of health and hygiene or for health control, the amount of the composition may be smaller than the lower limit of the above-specified range. In addition, even if the composition is used in an amount larger than the upper limit of the above range, it does not cause a problem in terms of safety.

There is no particular limit to the kind of food. Examples of foods to which the above material can be added include meats, sausages, bread, chocolate, candies, snack, confectionery, pizza, noodles, gum, dairy products including ice cream, various soups, beverages, teas, drinks, alcoholic beverages and multi-vitamin preparations. The foods include all health foods in a conventional sense.

The health beverage composition of the present invention may additionally contain various sweetening agents or natural carbohydrates as in conventional beverages. The natural carbohydrates include monosaccharides, such as glucose and fructose, disaccharides, such as maltose and sucrose, and natural sweeteners, such as dextrin and cyclodextrin. In addition, synthetic sweeteners, such as saccharin and aspartame, may be used. The amount of the natural carbohydrates in the beverage composition can be suitably selected by a person skilled in the art.

In addition, the composition of the present invention may contain various nutrients, vitamins, electrolytes, flavoring agents, colorants, pectic acid or its salt, alginic acid or its salt, organic acids, protective colloidal thickeners, pH adjusters, stabilizers, preservatives, glycerin, alcohol, carbonating agents used in carbonated drinks, etc. Additionally, the composition of the present invention may contain fruit flesh for the preparation of natural fruit juices, fruit juice beverages and vegetable juices. These components may be used alone or in combination. The contents of these additives in the composition can be suitably selected by a person skilled in the art.

In still another aspect, the present invention is directed to a method for preventing or treating neurological diseases, the method comprising a step of administering a composition comprising osmotin to an animal.

Examples of the subject to which the composition of the present invention can be administered include, but are not limited to, cattle, horses, elephants, pigs, rats, humans, deer, squirrels, rabbits, tigers, lions, wolves, goats, leopards, bears, whales, fur seals, bats, cats, sparrows, swallows, pheasants, hawks, eagles, swans, mallard ducks, penguins, doves, ostriches, emus, snakes, lizards, tortoises, crocodiles, frogs, toads, salamanders, crucian carps, catfishes, carps, snake fishes, basses, yellow corvinas, mackerels, sauries, hairtails, mandarian fishes, flatfishes, rock cods, stingrays.

Preferably, the treating or preventing method of the present invention can be achieved by inhibition of cytochrome-c release, a reduction in caspase expression, an increase in the Bcl-2/Bax ratio, or a decrease in $Ca^{2+}$ concentration.

The composition of the present invention may be administered alone or in combination with other therapeutic agents and may be administered simultaneously with or separately from a conventional therapeutic agent. In addition, the composition of the present invention may be administered in a single dose or multiple doses. It is important to administer the composition of the present invention in the minimum amount capable of obtaining the greatest effect without causing side effects in consideration of all the above factors, and this amount can be easily determined by a person skilled in the art.

Meanwhile, the composition of the present invention can be administered by any conventional route, as long as it can reach a target tissue. The composition of the present invention can be administered intraabdominally, intravenously, intramuscularly, subcutaneoulsly, intradermally, orally, intranasally, intrapulmonarily or intrarectally depending on the intended use, but is not limited thereto. The composition of the present invention can be administered by any device that can deliver the active ingredient into target cells.

Advantageous Effects

The composition comprising osmotin according to the present invention can inhibit the apoptosis of neurons to protect neurons from the external stimuli or toxicity that impairs the normal development and growth of neurons. Thus, the composition of the present invention is useful as a composition for preventing and treating neurological diseases.

MODE FOR CARRYING OUT THE INVENTION

Figure 1A:
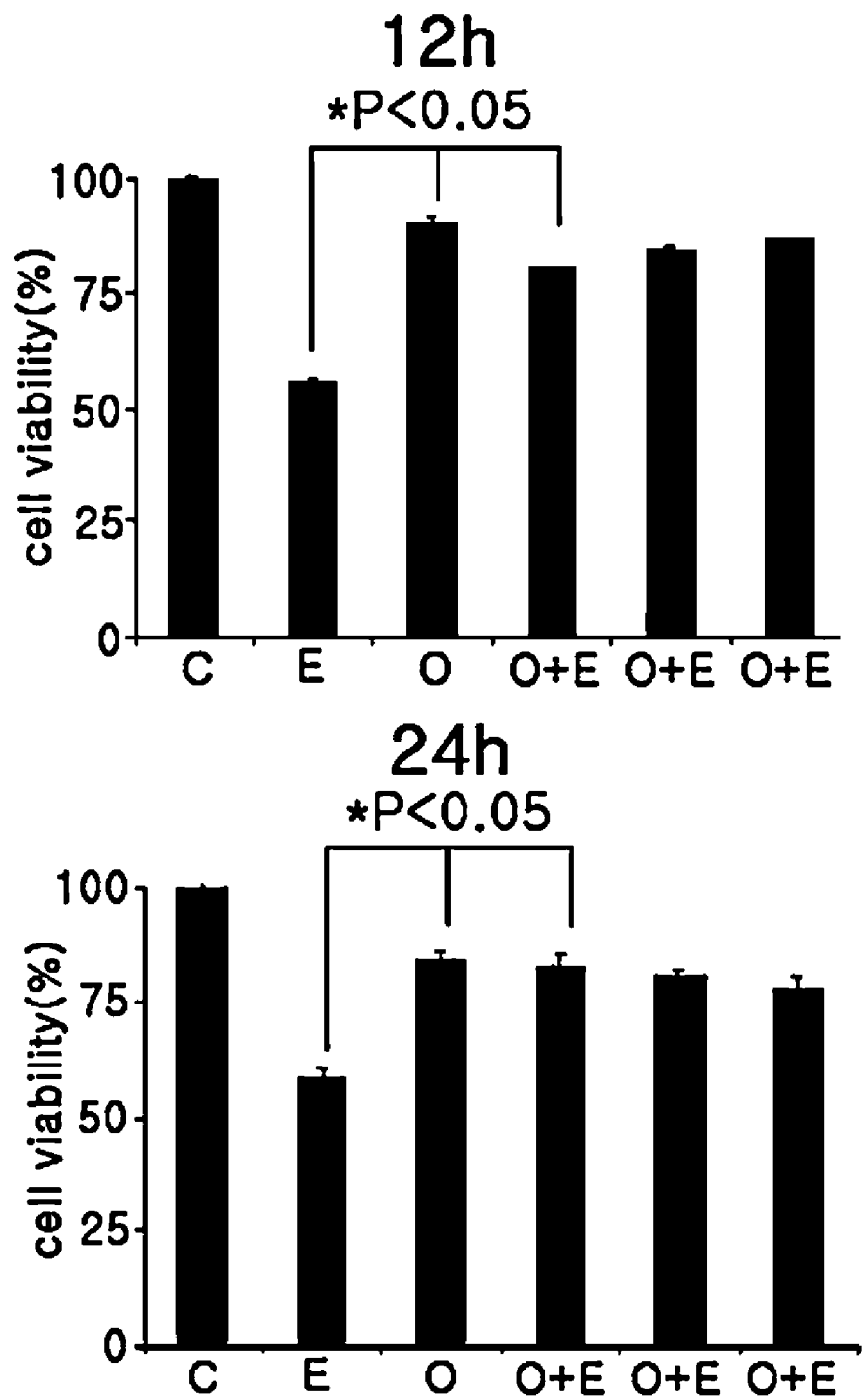
FIG. 1a shows the results of an MTT assay conducted by treatment with osmotin for 12 hours and 24 hours in order to examine the effect of ethanol on the survival of hippocampal neurons.

Hereinafter, the present invention will be described in further detail with reference to examples. It is to be understood, however, that these examples are for illustrative purposes only and are not intended to limit the scope of the present invention.

Example 1

Animal Treatment

Female (n=35) Sprague-Dawley rats (250 g; Neurobiological Laboratory, Gyeongsang National University) were housed in a temperature-controlled environment with lights from 06:00-20:00 h and with food ad libitum. The rats of experimental groups were treated with water.

The animals were randomly divided into two groups.

1. Timed pregnancy (the day of insemination equals to GD 0.5). Sprague-Dawley rats at gestational day 17.5 (GD 17.5) were injected intravenously with pentobarbital sodium (3 mg/100 g b.w), and then killed by decapitation.

2. Sprague-Dawley rats at postnatal day 7 (P7) were used in an in vivo experiment and equally divided into four different groups: a control group, an ethanol group, an osmotin group and an ethanol plus osmotin group. Rats at postnatal day 7 were injected subcutaneously with 5 g/kg of ethanol, and after 30 minutes, injected with a solution of 1 uM osmotin in saline. 12 hours after drug treatment, the rats were sacrificed.

Example 2

Primary Cell Culture and Drug Treatment

Tissue for culture was prepared from the hippocampus from rat at gestational day 17.5 (GD 17.5). The hippocampal tissue was treated with 0.25% trypsin-EDTA for 20 minutes and dissociated by mechanical trituration in cold calcium- and magnesium-free HBSS (Hank's balanced salt solution, pH 7.4). After pelleting by centrifugation, the cells were plated ($1 \times 10^6$ cells/ml) in cell culture plates pre-coated with poly-lysine (0.02 g/l) and chamber slides. The culture medium consisted of Dulbecco's modified Eagle medium (DMEM) containing 10% FBS (heat-inactivated fetal bovine serum), 1 mM pyruvate, 4.2 mM sodium hydrogen carbonate, 20 mM HEPES, 0.3 g/l bovine serum albumin, 50 U/ml penicillin, and 50 mg/l streptomycin. The cultures were maintained at 37° C. in a humidified atmosphere of 5% $CO_2$ and 95% air. After 5 days of culture, the hippocampal neuronal cells were treated with a normal medium and used as a control group, the experimental groups were treated with media containing 100 mM ethanol and 2 µg/ml (0.08 µM) osmotin, and the remaining three experimental groups including osmotin and ethanol were treated with 2, 4 and 6 µg/ml of osmotin, respectively. All the drug-treated groups were incubated in vitro for 24 hours.

Example 3

Western Blotting

Western blotting analysis was performed according to some modifications of a conventional method. In summary, primary cultured hippocampus cells were homogenized in cell lysis buffer (Cell signaling #9803) with 100 mM protease inhibitor PMSF. Immunoreactions were carried out either using anti-rabbit caspase-3, Bax, Bak, Bcl-2, Bcl-XL, caspase-9, cytochrome-c and PARP-1 (1:1000, 24 h, 4, Cell signaling, Santa Cruz) as antibodies or using rabbit-derived anti-goat AMPK and p-AMPK (1:1000, Santa Cruz, USA) as antibodies. Following rinses, horseradish peroxidase conjugated goat anti-rabbit or rabbit anti-goat (Santa Cruz) IgG-HRP (1:10000, Bio-Rad) was added and incubated for 60 min at room temperature. Proteins were detected by chemiluminescenceusing an ECL-detecting reagent (Amersham Pharmacia Biotech, Western blotting detection reagents) according to their protocol. The Western blots were analyzed by densitometry using the computer-based Sigma Gel (SPSS Inc. Chicago, USA). Density values were expressed as mean±SEM. One-way ANOVA analysis followed by Tukey-Kramer multiple-comparisons test was performed to determine the significance of differences between relevant treatment groups. In every case, the acceptance level for statistical significance was *$P<0.05$ and **$P<0.01$.

Example 4

MTT Assay

The logarithmic growth phase of primary neuronal cells was obtained by a growth assay using MTT (3-[4,5-dimethylthiazol-2-yl]-2,5-diphenly tetrazolium bromide). Hippocampal neuronal cells were cultured in a 96-well plate containing 200 µl of DMEM in normal medium at a concentration of $1 \times 10^5$ cells/well and used as a control group, and experimental groups were treated with media containing 100 mM ethanol, 2 µg/ml osmotin and different amounts of ethanol. The control group and the experimental groups were incubated at 37° C. for 24 hours in a humidified atmosphere of 5% $CO_2$. After incubation, cell viability was determined after treating each well with MTT (5 mg/ml in phosphate buffer saline, PBS) and incubating each well at 37 for 4 hours. Formazan crystals formed by viable cells were dissolved by adding DMSO to each well, and the absorbance was measured at a wavelength of 595 nm and recorded on a microtiter plate reader together with the results measured at a standard wavelength of 690 nm. OD (optical density) was calculated by the difference in absorbance between the standard wavelength and the experimental wavelength. The effect of the drug on growth was assessed by cell viability.

Example 5

Measurement of Mitochondrial Membrane Potential Using JC-1

Mitochondrial membrane potential was measured by a JC-1 mitochondrial membrane potential detection kit (Biotium Inc, Hayward, Calif., USA) according to the manufacturer's protocol. JC-1 emits green or red fluorescence, depending on mitochondrial membrane potential, green signal indicates depolarized mitochondria, and red signal indicates polarized mitochondria. Thus, a shift from red to green fluorescence is considered a reliable indication of a drop in mitochondrial membrane potential. In summary, neuronal cells were plated on culture plates pre-coated with poly-lysine (0.02 g/l) in a chamber ($1 \times 10^6$ cells/ml). The cell culture medium contained DMEM (Dulbecco's modified Eagle medium) containing 10% heat-inactivated FBS (fetal bovine serum), 1 mM pyruvate, 4.2 mM sodium hydrogen carbonate, 20 mM HEPES, 0.3 g/l BSA (bovine serum albumin), 50 U/ml penicillin and 50 mg/l streptomycin.

The cultures were maintained at 37° C. in a humidified atmosphere of 5% $CO_2$ and 95% air. After 3 days of culture, the neuronal cells were treated with a normal medium and used as a control group (C), and the media of the experimental groups were supplemented with 100 mM ethanol (E), osmotin, or osmotin plus ethanol. All the drug-treated groups were incubated in vitro at 37 for 24 hours. The drug-treated cells were harvested from the tertiary culture plates, stained with 19 JC-1 reagent at 37 for 15 minutes, and mixed twice with 1× assay buffer.

A change in mitochondrial membrane potential was measured using a FACSCalibur flow cytometer (Becton Dickinson, San Jose, Calif., USA) at a single cell level under the following conditions: FL1, 511 volt; FL2, 389 vole; FL1—10.5% FL2; FL2—25.9% FL1; 488 nm argon excitation laser and 585 nm band passage filter. A total of 10,000 cells were harvested and analyzed using CellQuest software version 3.0 (Becton Dickinson, San Jose, Calif., USA), and the number of cells at low mitochondrial membrane potential was quantified as percentage of the total cell group.

Example 6

Measurement of Intracellular $Ca^{2+}$

Intracellular $Ca^{2+}$ concentration was measured by the $Ca^{2+}$ fluorescence indicator acetoxymethylester fura-2 AM. Cortical cells ($1 \times 10^6$ cells in tertiary culture plates) were prepared as described above. The cortical cells were treated with normal medium and used as a control group, and the media of experimental groups were supplemented with 100 mM ethanol, 2 µg/ml osmotin, or osmotin and different amounts of ethanol. The cells were incubated in vitro for 5 days, and then washed twice with Krebs buffer, and incubated in a 5% $CO_2$ containing humidified incubator with 5 uM fura-2/AM-containing DMEM medium at 37 for 60 minutes.

The cells were washed twice with Locke solution (pH 7.8), and the fura-2 fluorescence signal of $[Ca^{2+}]c$ was measured using a luminescence spectrometer (LS50B, Perkin Elmer, Boston, Mass.). The light emitted from the Xenon lamp was excited between 340 nm and 380 nm bandpass filters, and fluorescence emitted at 510 nm was measured by a photon-measurement photoelectron-amplifying tube. The 340/380-nm fluorescence ratio was measured at 2 seconds or more. The obtained fluorescence signal was stored and analyzed either using a computer and general imaging software or using MicroVax II computer and software (origin 7). Intracellular calcium concentration was determined using a ratio method derived from the following Grynkiewicz equation:

$$[Ca] = K_d \times \frac{(R - R_{min})}{(R_{max} - R)} \times \frac{Sf2}{Sb2}$$

wherein $K_d$: the dissociation constant of fura-2-$Ca^{2+}$ interaction in 225 nM in the cytoplasm environment;
R: the fluorescence ratio at 340 nm and 380 nm;
$R_{min}$: the ratio when no $Ca^{2+}$ existed;
$R_{max}$: the ratio when $Ca^{2+}$ was saturated (using calcium chloride);
Sf2: the fluorescence at 380 nm when no $Ca^{2+}$ existed;
Sb2: the fluorescence at 380 nm when $Ca^{2+}$ was saturated.

Example 7

Detection of Apoptosis and Histological Analysis

FJB (Fluoro-Jade-B) staining was performed as previously described. In summary, it was performed using an immunofluorescence assay by incubating primary hippocampal cells at gestational day 17.5 (GD 17.5) in vitro on chamber slides pre-coated with poly-D-lysine. The hippocampal cells were treated with normal medium and used as a control group (C), and the media of experimental groups were supplemented with 100 mM ethanol (E), osmotin, or osmotin plus ethanol. All the drug-treated groups were incubated in vitro at 37 for 1 hour. The cultures were fixed with 4% paraformaldehyde-containing PBS for 5 minutes and stored at −70° C.

The next day, the slides were dried for 3 hours and dipped in 0.06% potassium permanganate solution for 10 minutes. After washing with water, the slides were dipped in 0.1% acetic acid and 0.0004% FJB solutions (Calbiochem, San Diego, Calif., USA) for 20 minutes. The slides were washed three times with distilled water and dried at 55° C. for 10 minutes. For imaging, the FITC filter of a confocal microscope (Fluoview Olympus, Japan) was used. PI-stained slides were prepared by dipping the slides in 1 µg/ml PI (propidium iodide)-containing PBS solution for 20 minutes with gentle mixing, and washing the slides twice with PBS for 10 minutes. Glass cover slips were mounted on glass slides with a mounting medium. FJB and PI staining was performed in vivo. Animals at postnatal day 7 were anesthetized with sodium pentobarbital (50 mg/g. i.p). The brains removed from the fetus were fixed in cold 4% NBP for 48 hours and cryoprotected in 20% sucrose phosphate buffer for 48 hours at 4° C. Whole fetuses were frozen at O.C.T compound (A.O. USA), and 14 µm sections were made in the coronal planes. Sections were thawed and mounted on the probe-on positively charged slide (Fisher). Slides were dipped in 1 µg/ml of PI solution in PBS for 20 min at room temperature with gentle mixing and washed twice with PBS for 10 min. Glass cover slips were mounted on glass slides with a mounting medium. A PI filter was used to detect the PI staining (Red color), and an FITC filter was used to detect Fluoro-Jade-B (Green color). For images, the present inventors used a Zeiss fluorescent microscope (Zeiss, Germany) and a confocal microscope (Olympus, Japan). Photographs were taken with a soft imaging systems video camera.

Example 8

Visualization of Mitochondrial Cytochrome-c Release and Capase-3 Expression

The brains of rats at postnatal day 7 were treated with the drug for 4 hours, and then the in situ analysis of cytochrome-c release and caspase-3 expression was carried out by an immunofluorescence assay.

Young rats in the developmental stage were perfused with 4% paraformaldehyde and then transcardially perfused with 1×PBS, and the brains were fixed in 4% paraformaldehyde overnight and then dipped in 20% sucrose until the brains settled down to the bottom of the tube. Whole fetuses were frozen at O.C.T compound (A.O. USA), and 16 μm sections were made in the coronal planes. Meanwhile, primary cultured hippocampal neuronal cells ($1 \times 10^6$ cells on culture plates) treated with ethanol, osmotin or ethanol plus osmotin were fixed 4% NBP (neutral buffer paraformaldehyde) and washed with PBS in chilled conditions. Cytochrome-c was detected by using mouse anti-cytochrome-c antibody (1:250, Santa Cruz Biotechnology, CA, USA) overnight at 4° C. and rabbit anti-mouse FITC-labeled antibody for 90 min at room temperature (1:100, Santa Cruz Biotechnology, CA, USA).

Subsequently, caspase-3 expression was detected by using rabbit anti-caspase-3 antibody (1:250, Cell signaling) overnight at 4° C. and goat anti-rabbit TRITC-labeled antibody (1:100, Santa Cruz Biotechnology, CA, USA) for 90 min at room temperature with no light. Slides were mounted with Prolong Antifade reagent (Molecular Probes, Eugene, Oreg., USA). Cytochrome-c (green) and caspase-3 (red) staining patterns were acquired by use of a confocal laser scanning microscope (Fluoview FV 1000, Olympus, Japan).

Example 9

Data Analysis and Statistics

The object band from RT-PCR and Western blotting were scanned and analyzed by densitometry using a computer based on the Sigma Gel System (SPSS Inc., Chicago, Ill.). Density values were expressed as mean±SEM. One-way ANOVA analysis followed by Tukey-Kramer multiple-comparisons test was performed to determine the significance of differences between relevant treatment groups. In every case, the acceptance level for statistical significance was *$P<0.05$ and **$P<0.01$.

Results

Osmotin Inhibits Ethanol-Induced Neurodegeneration of Neuronal Cells

Figure 1B:
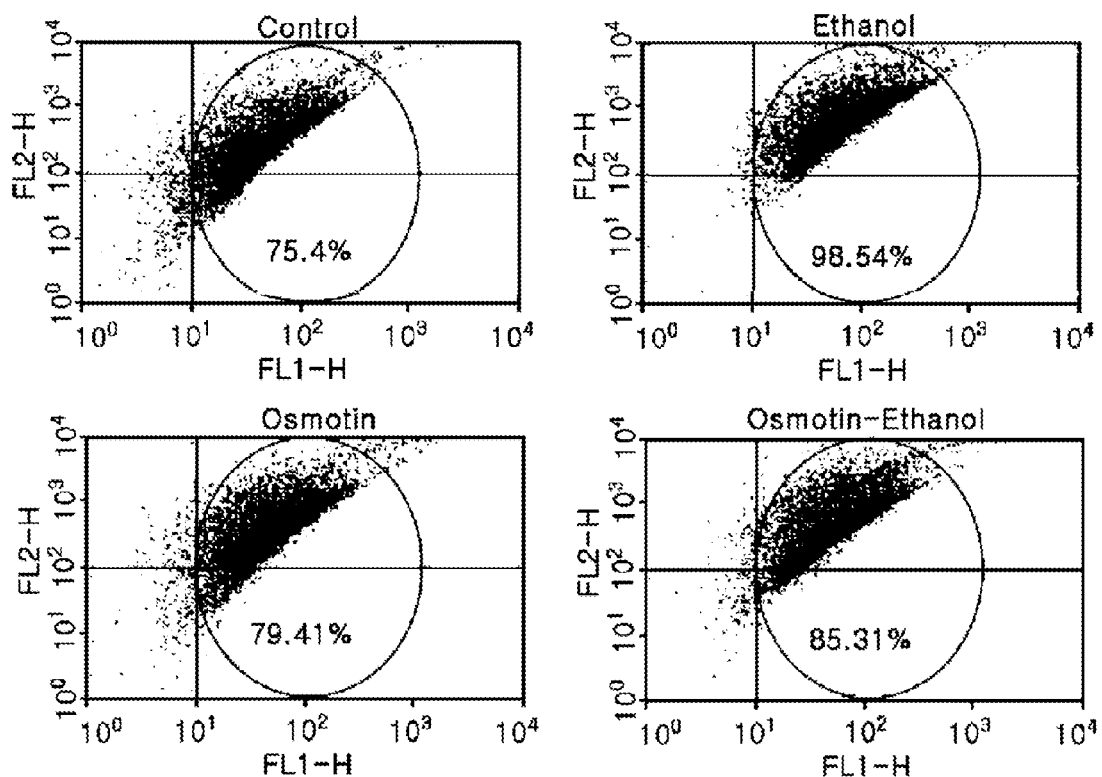
FIG. 1b shows the results of flow cytometry of mitochondrial membrane potential by JC-1 staining after treatment with ethanol, osmotin, and osmotin plus ethanol for 12 hours and 24 hours.

In order to examine whether osmotin protects primarily cultured neuronal cells from apoptotic neurodegeneration, the present inventors performed the above-described experiments. In addition, an MTT assay was used to evaluate the role of osmotin in protecting cells from ethanol toxicity in neuronal cells treated with ethanol and three different concentrations of osmotin. In these experiments, the concentrations of ethanol and osmotin make it possible to evaluate the cytotoxicity of ethanol and the role of osmotin in protecting cells from ethanol toxicity. The cells exposed to osmotin, ethanol, or osmotin plus ethanol for 12 hours and 24 hours showed a significant increase in cell viability compared to the group treated with ethanol alone. As a result, the cells treated with osmotin plus ethanol after 12 hr and 24 hr of culture showed a significant increase in cell viability compared to the control group, suggesting that osmotin can significantly inhibit the effect of ethanol (FIG. 1a). Each bar in FIG. 1a indicates the mean of three independent experiments (n=3) carried out with 3 plates. The mitochondrial membrane potential in the group treated with ethanol, osmotin or ethanol plus osmotin was measured using the fluorescent dye JC-1. JC-1 obtained from mitochondria was observed with a flow cytometer. In the flow cytometry, the loss of mitochondrial membrane potential is related to an increase in FL1 fluorescence (FIG. 1b). As can be seen in FIG. 1b, when neuronal cells were treated with ethanol, a visible cell subpopulation appeared together with low mitochondrial membrane potential. On the other hand, the group treated with ethanol plus osmotin showed the restoration of mitochondrial membrane potential compared to the ethanol-treated group.

Osmotin Inhibits Ethanol-Induced Apoptosis in Hippocampal Neuronal Cell Culture

Figure 2A:
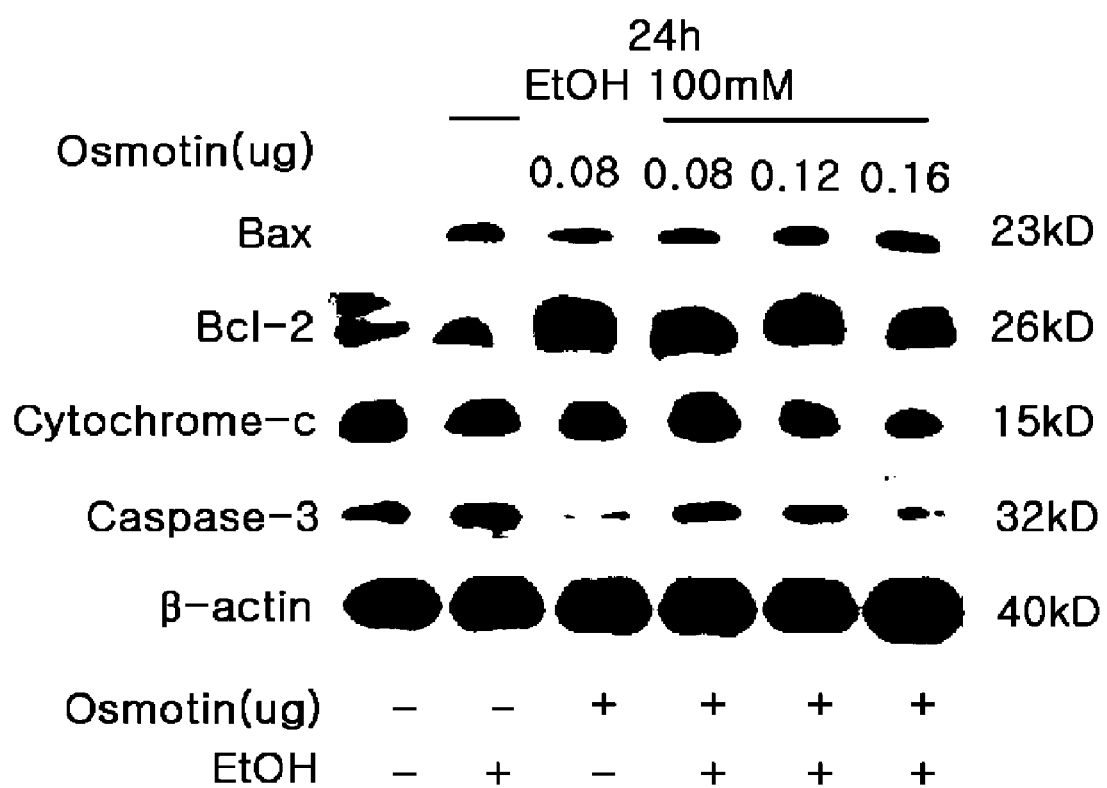
FIG. 2a shows the results of immunoblotting of Bax, Bcl-2, cytochrome-c and caspase-3 after 24-hr treatment with ethanol, osmotin, and osmotin plus ethanol.
Figure 2B:
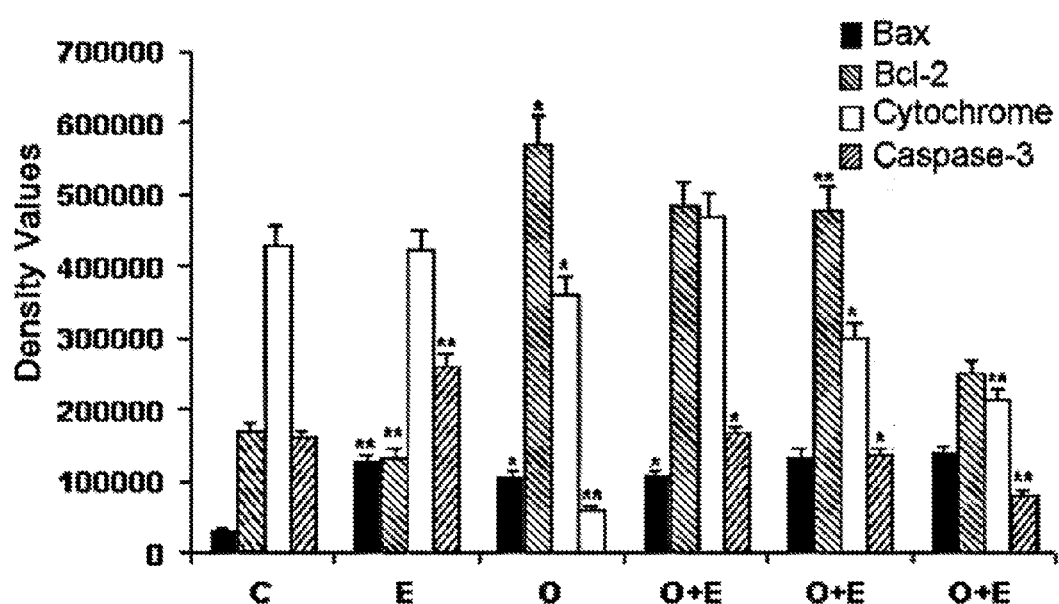
FIG. 2b shows density values (expressed as ±S.D. (n=4)) corresponding to Bax, Bcl-2, cytochrome-c and caspase-3.

In order to understand the protective effect of osmotin against ethanol at a molecular level, the present inventors performed Western blotting with primarily cultured hippocampal neuronal cells. As can be seen in FIGS. 2a and 2b, the apoptosis stimulating protein Bax was significantly induced after exposure to ethanol, and significantly decreased upon treatment with osmotin. On the other hand, Bcl-2 significantly increased in a concentration-dependent manner when the cells were treated with ethanol plus osmotin, suggesting that the anti-apoptotic effect of osmotin against ethanol is induced by an increase in Bcl-2 protein that plays an important factor of the anti-apoptotic effect against ethanol (FIGS. 2a and 2b).

When the cells were treated with ethanol, the active ingredient of cleaved caspase-3 appeared in Western blotting; however, the group treated with ethanol plus osmotin showed a decrease in the expression of caspase-3 compared to the ethanol-treated group. The event upstream of the caspase chain reaction is the release of cytochrome-c from mitochondria. Osmotin inhibits cytochrome-c release in a dose-dependent manner, whereas ethanol induces the release of cytochrome-c.

Osmotin cytochrome-c, which inhibits the ethanol-induced release of cytochrome-c, the ethanol-induced activation of caspase-3 and the ethanol-induced overexpression of intracellular $Ca^{2+}$ in neuronal cells, is a mitochondrial inner membrane protein, and when a large amount of the protein is released from the cytoplasm, a chain reaction occurs, resulting in the activation of caspase-3. Thus, the present inventors examined the migration of cytochrome-c and the activity of caspase-3 using a confocal microscope. As a result, the diffused staining distribution of cytochrome-c (green FITC-labeled) was observed, suggesting that the cytochrome-c was released from mitochondria, like capase-3 (TRITC, red), when the hippocampal neuronal cell culture was treated with ethanol or ethanol plus osmotin. As can be seen in FIG. 3, the exposure of hippocampal neuronal cells to ethanol is responsible for the increases in expressions in cytochrome-c and caspase-3 compared to the control group. The group treated with ethanol plus osmotin showed significant decreases in the expressions of cytochrome-c and caspase-3, suggesting that osmotin prevents cytochrome-c from being released from cytoplasm to induce apoptosom.

Figure 3A:
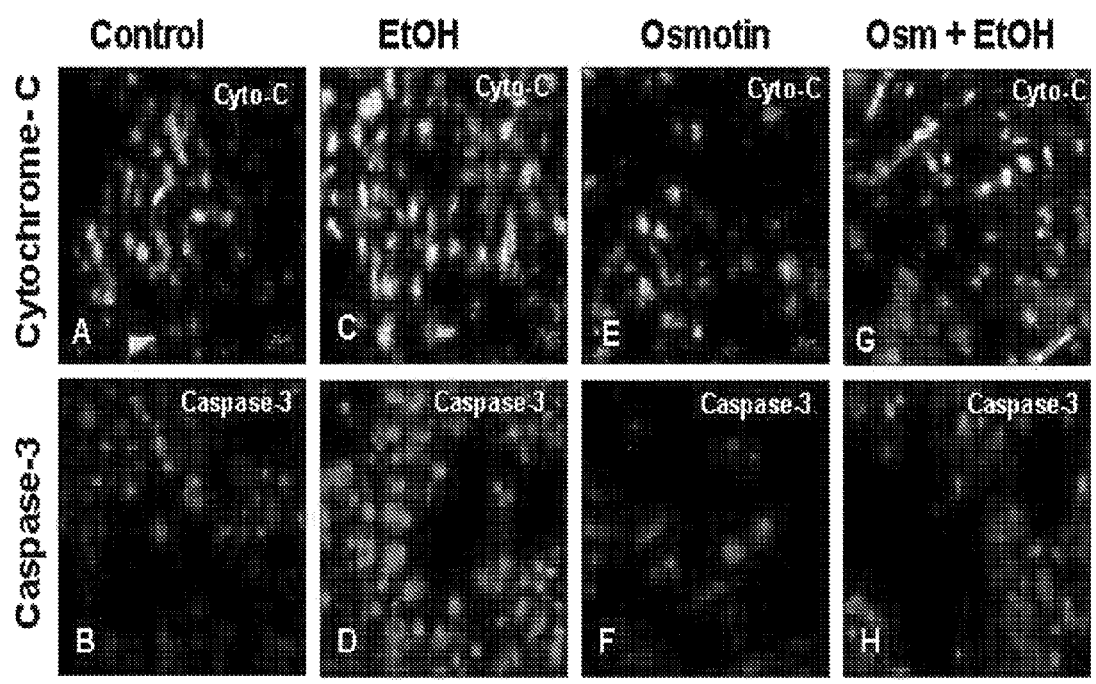
FIG. 3a shows the results of analyzing the expressions of cytochrome-c and caspase-3 in the hippocampal neurons of pregnant rats by immune fluorescence in situ.
Figure 3B:
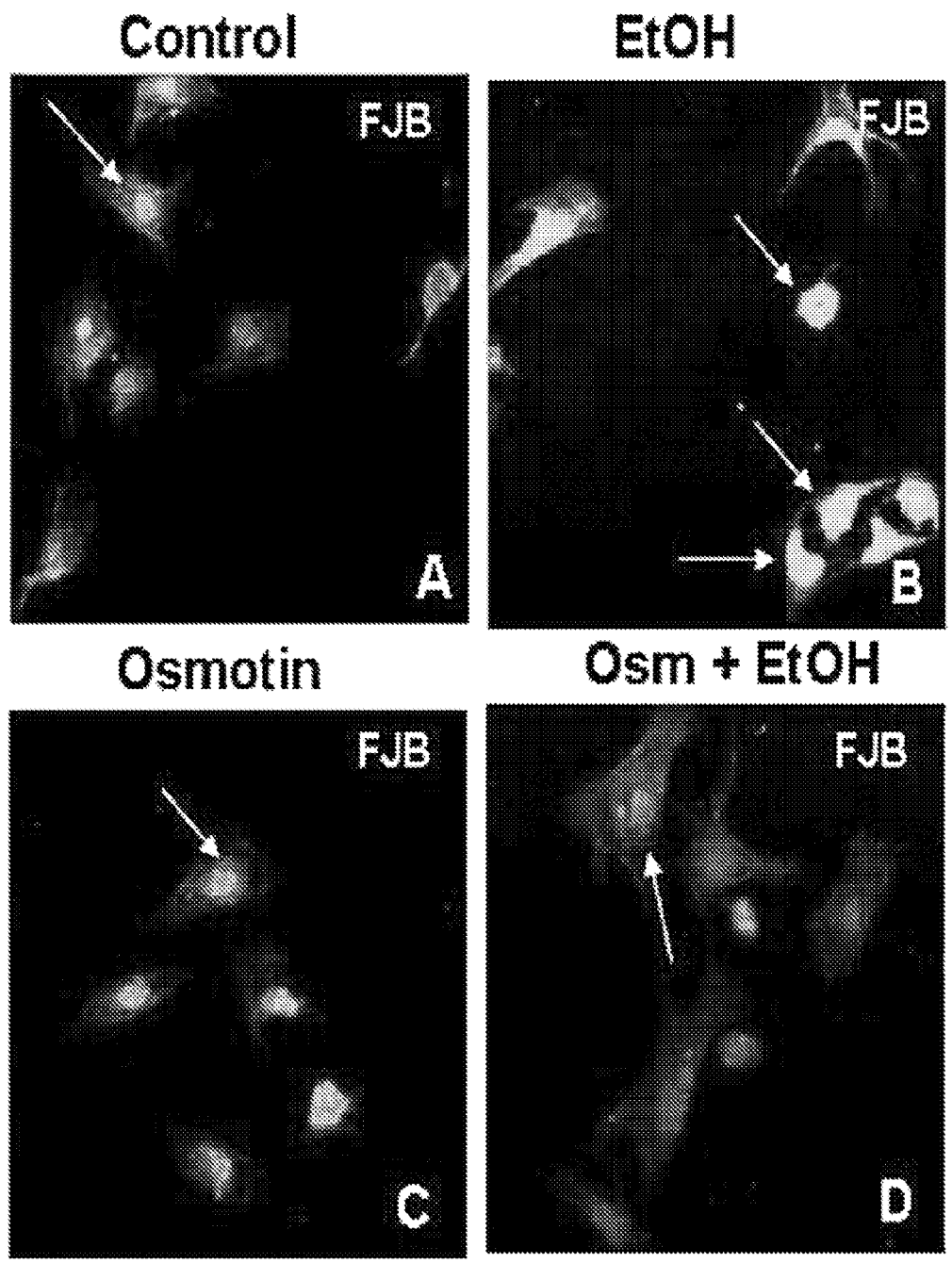
FIG. 3b shows the results of FJB staining of hippocampal neuronal cultures exposed to ethanol, osmotin, and ethanol plus osmotin.
Figure 3C:
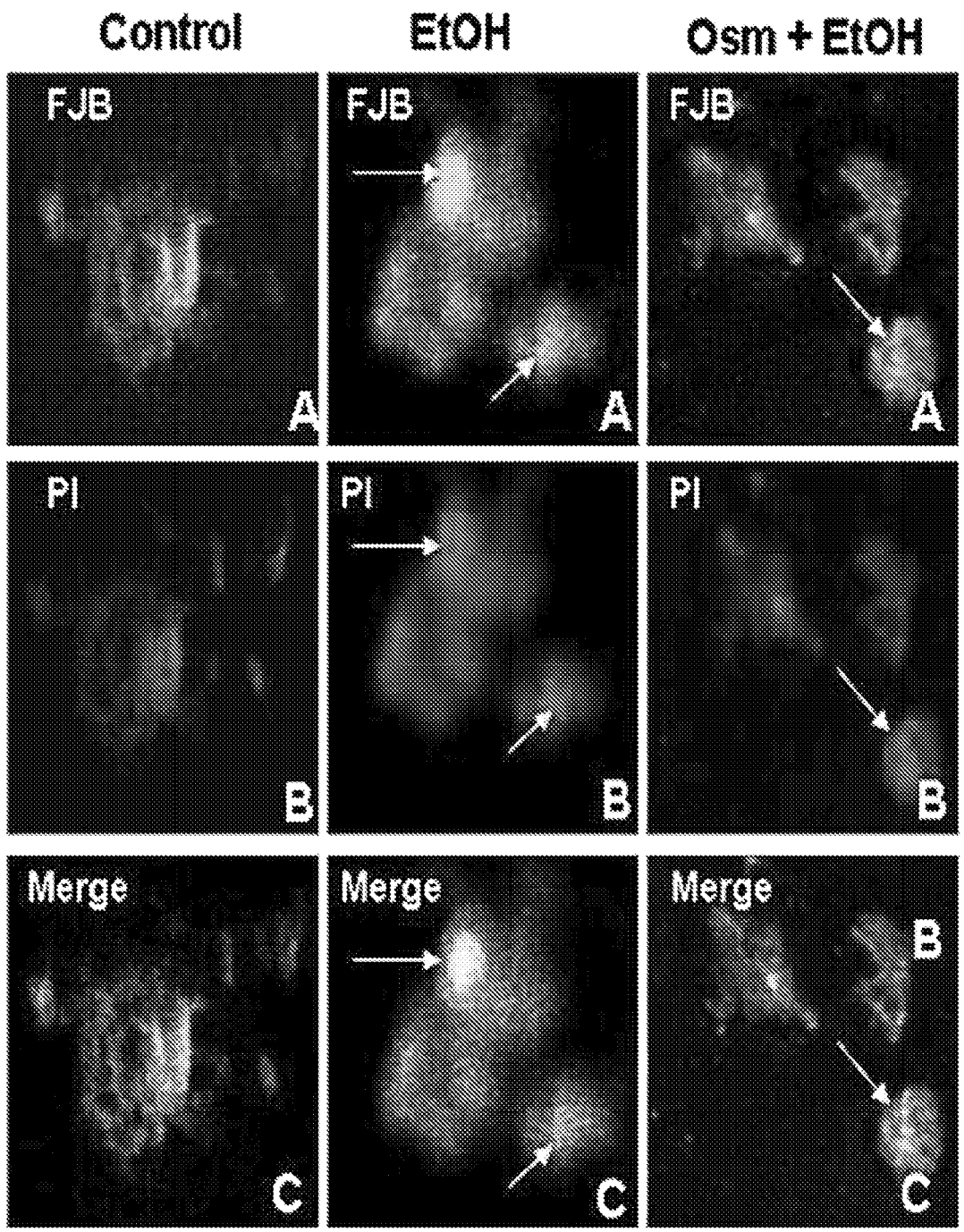
FIG. 3c shows the results of immunofluorescence analysis of PI- and FJB-labeled neurodegeneration in the hippocampal neuronal cells of pregnant rats.

FJB staining is a reliable marker for examining the brittleness of neuronal cells after the survival period and was used to identify degenerating neurons. FJB was used to observe the amount of FJB-positive cells and the morphology of neuronal cells treated with ethanol, osmotin or osmotin plus ethanol (FIG. 3). In the experimental results, the cells treated with ethanol were significantly concentrated and showed an increase in FJB-positive cells. In contrast, the cells treated with osmotin and the cells treated with ethanol plus osmotin showed a decrease in the amount of FJB-positive cells, and the cell morphology was similar to that of the control group. These results are consistent with the results of Western blotting, MTT assay and flow cytometry. Thus, the induction of neurodegeneration significantly increased in the cells treated with ethanol compared to in the cells treated with ethanol plus osmotin (FIG. 3). After ethanol treatment, FJB and PI staining was performed in order to determine the effect of osmotin on neuronal cells. FJB and PI staining showed the neurogeneration of ethanol-treated cells in the brain, which is a major marker of neuronal injury. In contrast, the cells treated with ethanol plus osmotin showed a decrease in the FJB and PI labeling, and these results are consistent with the results of MTT assay and flow cytometry. Thus, the induction of neurodegeneration significantly increased in the ethanol-treated cells compared to in the cells treated with ethanol plus osmotin (FIGS. 3b and 3c). The traces of apoptosis were quantified by measuring intracellular $Ca^{2+}$ levels in neuronal cells.

Figure 3D:
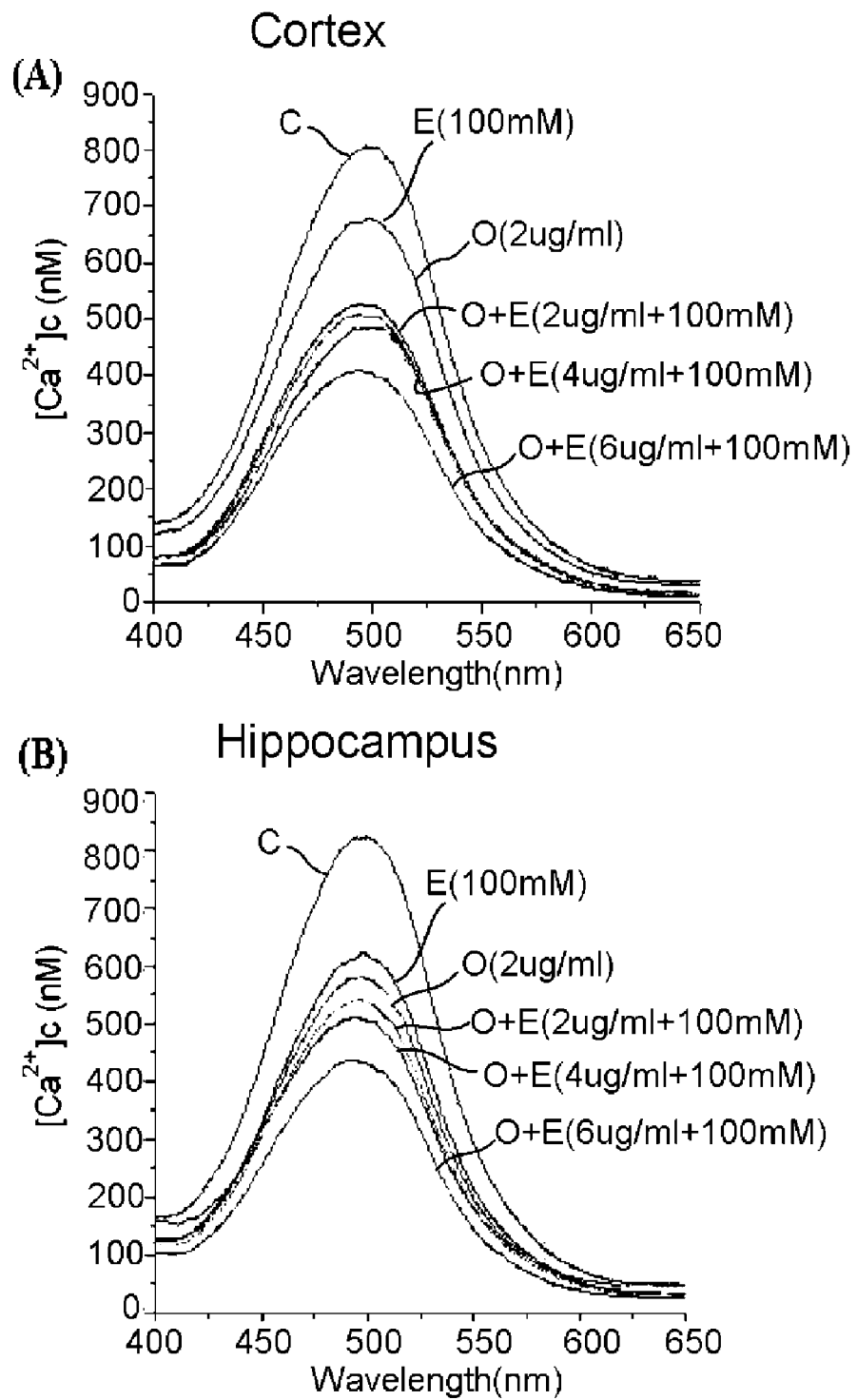
FIG. 3d shows the comparative analysis of PI and FJB in the hippocampal area.

The $Ca^{2+}$ levels are the prerequisites for post-mitochondrial events including caspase activation and programmed cell death (PCD). The generation of an intracellular $Ca^{2+}$ signal includes a variety of molecular chain reactions depending on the kind of cell. Researchers paid attention to the role and mechanism of $Ca^{2+}$ signal in the neuron of CNS. The change in the $Ca^{2+}$ concentration of the cytoplasm is important in neurotransmitter release, efficient synapse transmission, and neurodevelopment, and the activation of apoptosis stimulating pathways resulting from difficulty in the regulation of $Ca^{2+}$ homeostasis was proposed as a mechanism based on ethanol toxicity. Thus, it is important to examine the change in $Ca^{2+}$ levels of cells exposed to ethanol, osmotin, or ethanol plus osmotin. The present inventors examined the levels of $Ca^{2+}$ in the control group and each experimental group, and as a result, it was seen that the levels of $Ca^{2+}$ in the cortical and hippocampal neuronal cells of the early developmental stage significantly increased due to ethanol compared to the control group (FIG. 3d). However, osmotin showed the results contrary to those of ethanol by maintaining the homeostasis of the early developmental stage.

Osmotin Inhibits Ethanol-Induced Apoptosis Pathway in Brain of Developmental-Stage Rats 7-day-old Sprague-Dawley rats were injected with 5 g/kg of 20% ethanol-containing saline and sacrificed at varying points of time. The blood ethanol level was maintained at 200 mg/dl or more for several hours, and the above level is a minimum concentration capable of inducing neurodegeneration as previously described in Olney et al., 2002b and Carloni et al., 2004. This concentration is equal to the concentration in a human fetus after administration of an excessive amount of ethanol into the mother. 4 hours of intraperitoneal injection of ethanol, apoptotic neurodegeneration was observed and maintained for 20 hours.

Figure 4A:
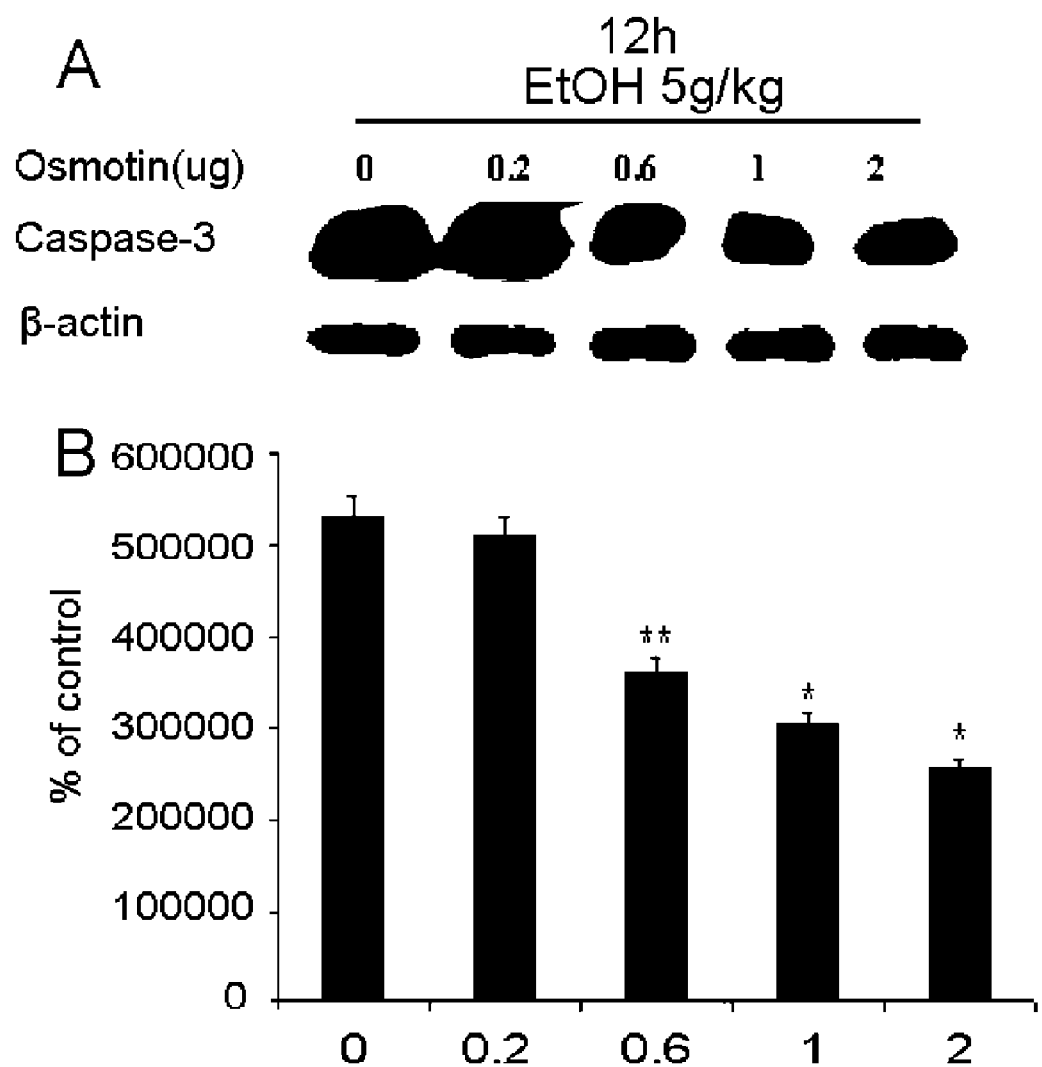
FIG. 4a shows that osmotin inhibits caspase-3 activity induced by ethanol.

In order to determine whether osmotin can inhibit the ethanol-induced activation of caspase-3, osmotin was administered at increasing doses after ethanol exposure. Administration of osmotin reduced the activity of caspase-3 after 12 hours, and the maximum inhibition of caspase-3 activity could be seen at a dose of 0.20 μg/g (or 2 ug/10 g) (FIG. 4a). Based on such results, in a subsequent experiment, 5 g/kg of ethanol was administered, and after 30 minutes, 0.20 μg/g of osmotin was administered.

In order to examine the molecular mechanism of neurodegeneration resulting from ethanol-induced apoptosis and the protective effect of osmotin, the changes in apoptotic proteins related to the mitochondrial pathway were observed. 12 hours after treatment with ethanol and osmotin, the expressions of Bax and Bcl-XL proteins in the cortex and hippocampus of the brain, including apoptosis-stimulating Bax and anti-apoptotic Bcl-2, members of the Bcl-2 family, were observed by Western blotting. When the brains of developmental-stage rats administered with ethanol and then treated with osmotin, the excessive control of Bax protein was reverted. The overexpression of Bax is known to induce mitochondrial dysfunction and cell death, and in this experiment, exposure to ethanol induced the overexpression of Bax in cells. On the other hand, treatment with ethanol plus osmotin inhibited the overexpression of Bax and contributed to the neuron protective effect of preventing ethanol-induced neurodegeneration in developmental-stage rats. The expressions of Bax and Bak in the hippocampus and cortex of developmental-stage rats at 12 hours after ethanol administration were up-regulated compared to those of the control group. However, in the case of treatment with osmotin (5 μg/g), the up-regulation of Bax was reverted (FIG. 4b (A and B)). Administration of ethanol for 12 hours showed that the Bax/Bcl-2 ratio in the brain of developmental-stage rats increased and that significant apoptosis was induced. On the other hand, when osmotin (5 μg/g) was administered, the Bax/Bcl-2 ratio significantly decreased and anti-apoptosis was induced (FIG. 4b (A and B)).

Osmotin cytochrome-c which inhibits the ethanol-induced release of cytochrome-c from mitochondria is a mitochondrial inner membrane protein, and the release of a large amount of the protein from cytoplasm results in a chain reaction that activates caspase-3. The mitochondrial apoptotic chain reaction requires the release of the mitochondrial inner membrane protein cytochrome-c into cytoplasm, and increased cytochrome-c in cytoplasm induces the activation of caspase-9 and caspase-3, resulting in neuronal death. As a marker for the activation of the mitochondrial chain reaction, the protein levels of cytochrome-c in the hippocampus and cortex were measured. It was observed that the levels of Bax in both the hippocampus and cortex of the brain of developmental-stage rats increased, and these increases are associated with an increase in the level of cytochrome-c in cytoplasm after ethanol administration (FIG. 4b (C and D)).

Figure 4B:
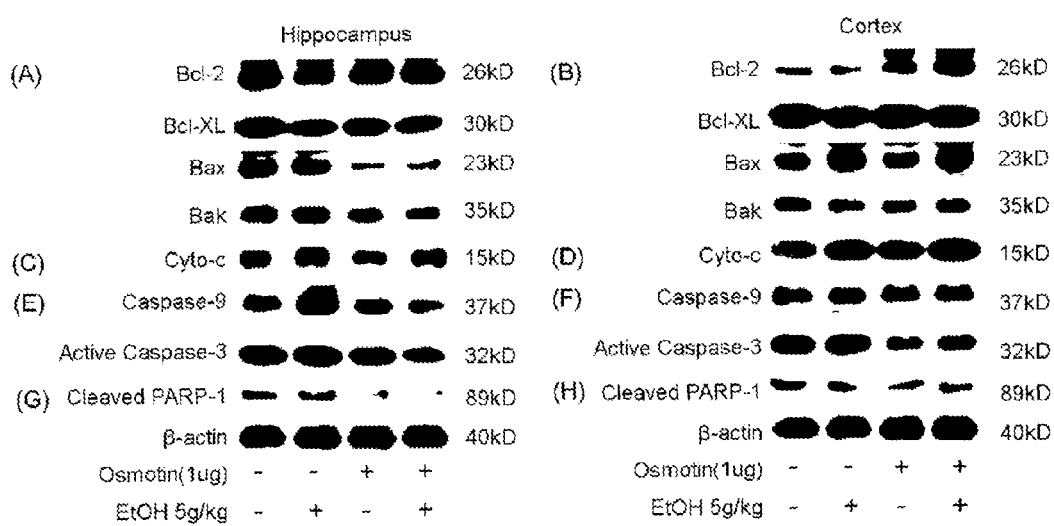
FIG. 4b shows the results of Western blotting of Bax, Bak, Bcl-2, Bcl-XL, cytochrome-c, caspase-9, caspase-3 and PARP-1, conducted after 30-min administration of osmotin following 12-hr administration of ethanol.

When the control group was compared with the osmotin-treated group, the expressions of cytochrome-c in the hippocampus and cortex of the brain significantly decreased 12 hours after treatment with ethanol plus osmotin (FIG. 4b (C and D)).

Osmotin caspase activity of inhibiting the ethanol-induced activation of caspase-9 and caspase-3 in the brains of developmental-stage rats is the characteristic of general apoptosis pathways, and the release of cytochrome-c activates caspase-3, resulting in mitochondrial destruction, deficiency of cellular energy, cleavage of cytoskeletal elements, and destruction of cell proteins. In order to examine the abilities of osmotin to prevent the depolarization of a mitochondrial membrane and the release of cytochrome-c, the present inventors examined downstream cellular pathways such as the inhibition of caspase-9 and caspase-3. Specifically, to measure the levels of activated caspase-9 and caspase-3 in the hippocampus and cortex, Western blot analysis was used. As a result, in the ethanol-treated group, both the levels of caspase-9 and caspase-3 in the hippocampus and cortex of the brain significantly increased. However, in the group treated with osmotin following ethanol exposure, the levels of the two activated caspases in the hippocampus and the cortex significantly decreased to the extents similar to those of the control group or the osmotin-treated group (FIG. 4b (E and F)).

It is known that osmotin ethanol which inhibits the ethanol-induced digestion of PARP-1 in the brains of developmental-stage rats induces a rapid increase in ROS that induces DNA fragmentation and cell death. Despite DNA restoration resulting from PARP-1 activity which is observed in neuronal cytotoxicity, PARP-1 is one of early targets of caspase-3.

Thus, the present inventors examined the cleavage of PARP-1 protein by Western blot analysis. As a result, it was seen that the cleavage of PARP-1 in the cortical and hippocampal neurons of developmental-stage rats is attributable to an increase in caspase-3 activity. Furthermore, the levels of cleaved PARP-1 in the cortex and hippocampus of osmotin-treated rats significantly increased compared to those of the control group. The effect of osmotin after ethanol administration visibly reduced the cleavage of PARP-1 (total length: 116 KDa) and involved a decrease in a 89 KDa caspase-3 (cleavage product) in the cortex and hippocampus of developmental-stage rats. Thus, in the hippocampus and cortex of the brain of developmental-stage rats, the cleavage of PARP-1 increased, whereas in the case of treatment with osmotin plus ethanol, the levels of cleaved PARP-1 in both the hippocampus and the cortex decreased. Such results were similar to those observed in the osmotin-treated group or the control group (FIG. 4b (G and H)).

Figure 5A:
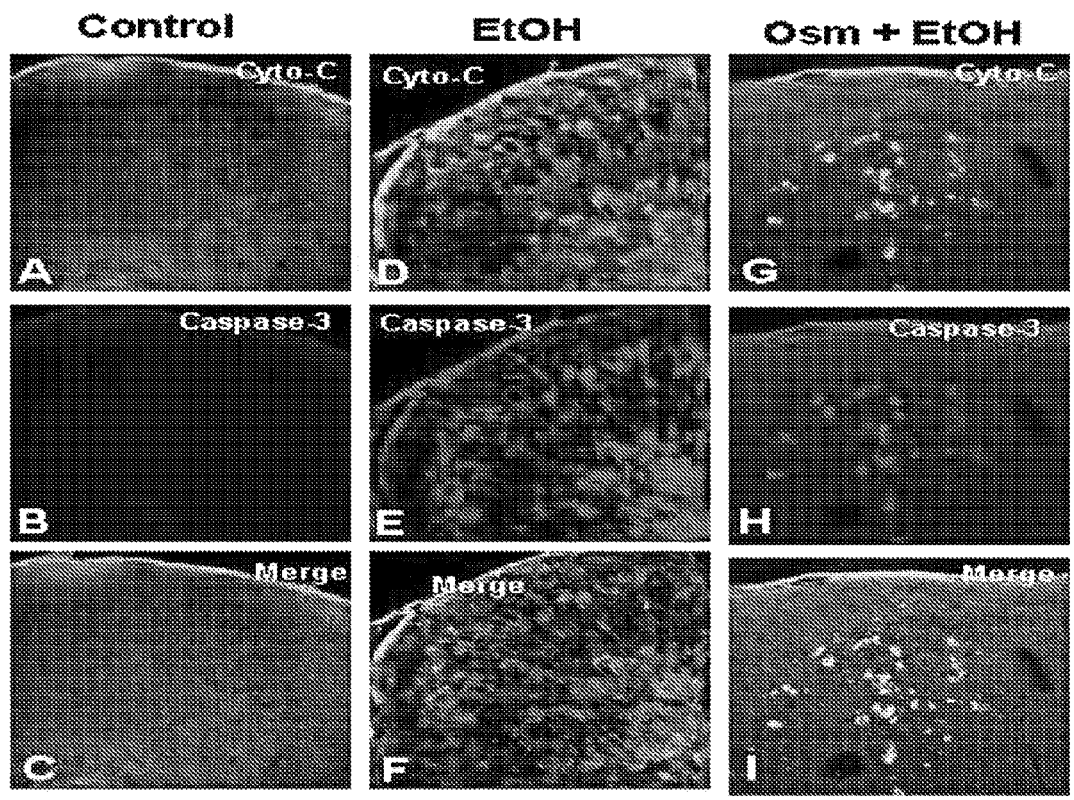
FIG. 5a shows the results of visualizing mitochondrial cytochrome-c release and caspase-3 expression in the brain cortex.
Figure 5B:
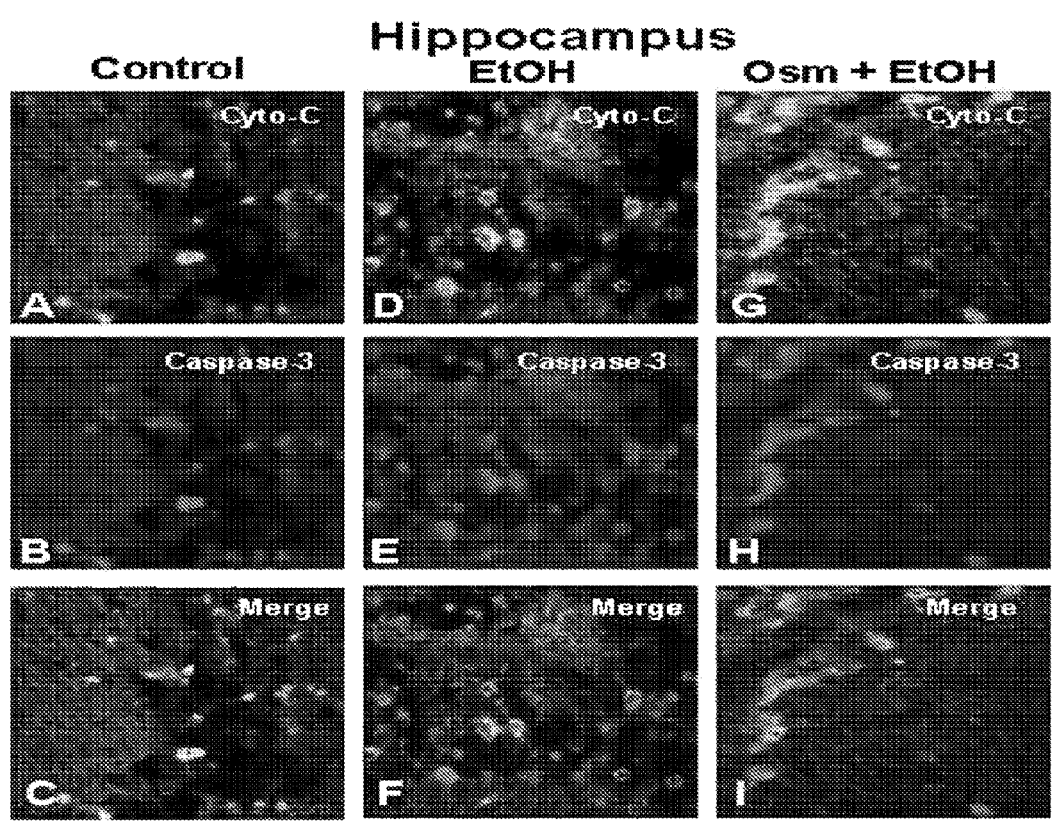
FIG. 5b shows the results of visualizing mitochondrial cytochrome-c release and caspase-3 expression in the CA1 region of the brain hippocampus.

Visualization of Mitochondrial Cytochrome-c Release, Caspase-3 Expression and Tissue Structure In order to determine whether osmotin inhibits cytochrome-c release and caspase-3 activity, osmotin sufficient for preventing ethanol-induced apoptotic cell death was used, and the brain was histologically analyzed using an immunofluorescence assay. The degree of ethanol-induced neurodegeneration and the neuron protective effect of osmotin on ethanol-induced neuronal death were analyzed in the cortex and hippocampus of the brains of developmental-stage rats (FIGS. 5a and 5b). Ethanol induced the release of cytochrome-c (green FITC-labeled) together with caspase-3 (TRITC-labeled, red) from mitochondria, whereas treatment with osmotin plus ethanol showed decreases in the expression of caspase-3 in the hippocampus and cortex of the brain and the release of cytochrome-c from mitochondria, suggesting that osmotin inhibits the effects of ethanol. The merged photographs indicate cytochrome-c release and caspase-3 expression in cytoplasm and shows the results of treatment with ethanol and ethanol plus osmotin in the brains of developmental-stage rats (FIGS. 5a and 5b).

Figure 6A:
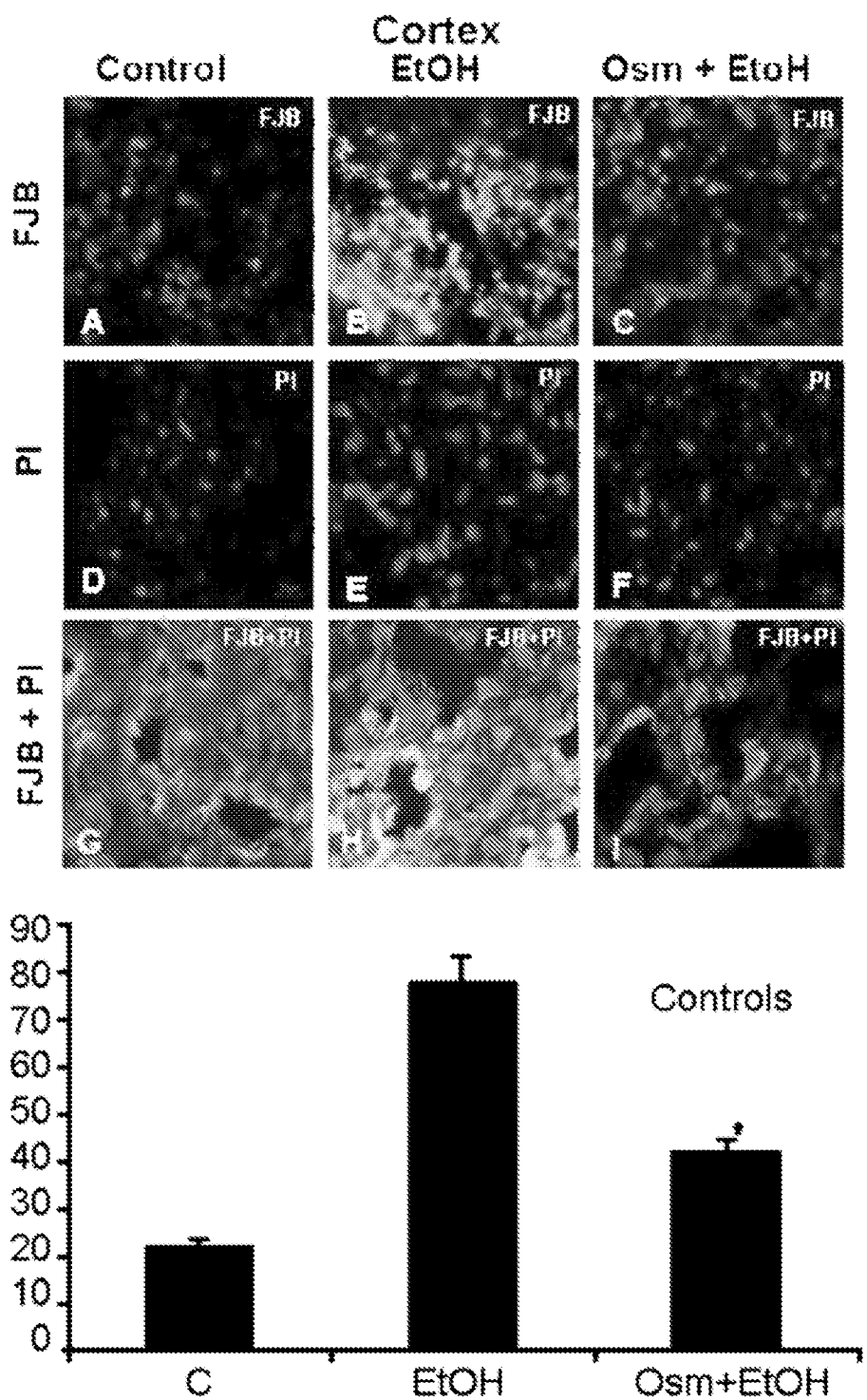
FIG. 6a shows the results of PI- and FJB-staining of neurodegeneration in the cortex of the brains of rats after administration of ethanol and osmotin.
Figure 6B:
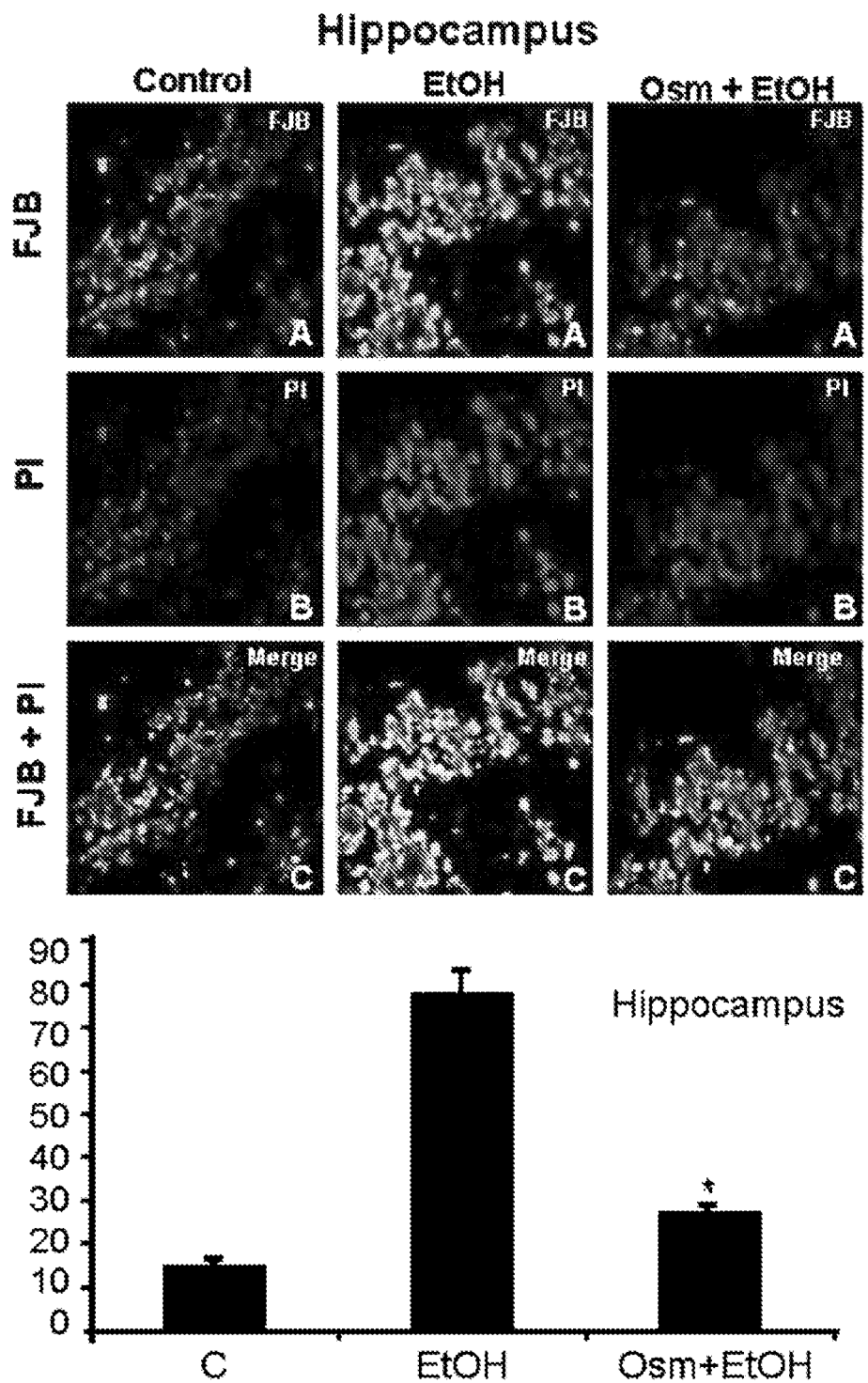
FIG. 6b shows the results of PI- and FJB-staining of neurodegeneration in the hippocampus of the brains of rats after administration of ethanol and osmotin.

In order to evaluate whether osmotin ethanol which reduces the severity of ethanol-induced neurodegeneration in the brains of developmental-stage rats induces the death of neuronal cells in vivo and whether osmotin has contrary effects in the cortex and hippocampus of the brain, histological analysis was performed using PI and FJB. PI is a nucleic acid stain usually used as a counter stain in multicolor fluorescence techniques. In tissue sections, it is used as a nuclear marker and sometimes employed to identify nuclei showing apoptotic changes. On the other hand, FJB staining is a reliable marker for examining the brittleness of neuronal cells after the survival period and was used to identify degenerating neurons. Confocal microscopic analysis revealed that there was a robust staining in the cortex and hippocampus of the brains of rats after ethanol treatment as compares to the control group (FIGS. 6a (A-I) and 6b (A-C)). In hippocampal CA1 subfields, large neurons were scattered and shrunken, and the nuclei were markedly condensed (FIGS. 6b (A-C)). The results of FJB and PI staining showed a significant increase in FJB and PI staining in the cortex and hippocampus of rats of the ethanol-induced neurodegeneration model as compared to the saline-treated group (FIGS. 6a and 6b). At 12 hours after osmotin administration, neurodegeneration appeared in the anterior cingulate cortex and the hippocampal CA1. In the experiment for the anterior cingulate cortex and the hippocampal CA1 using FJB, there was an increase in the number of FJB-positive cells (FIGS. 6a, panels (A-I), panels (A-C)). In contrast, young rats treated with osmotin following ethanol showed a significant decrease in the number of FJB-positive cells in the brain as compared to the control group. The anterior cingulate cortex and hippocampal CA1 of the ethanol-treated group showed increased vacuolization, neuronal loss and tissue injury, and neurodegeneration increased in the hippocampus and cortex of the ethanol-treated group as compared to the control group. In other words, in the group treated with osmotin following ethanol, osmotin showed decreases in vacuolization and neuronal loss and showed significant neuronal protection against the ethanol-induced apoptosis and neuronal death as compared to the control group that appeared to be morphologically normal (FIGS. 6a and 6b, panels (A and C)).

Figure 6C:
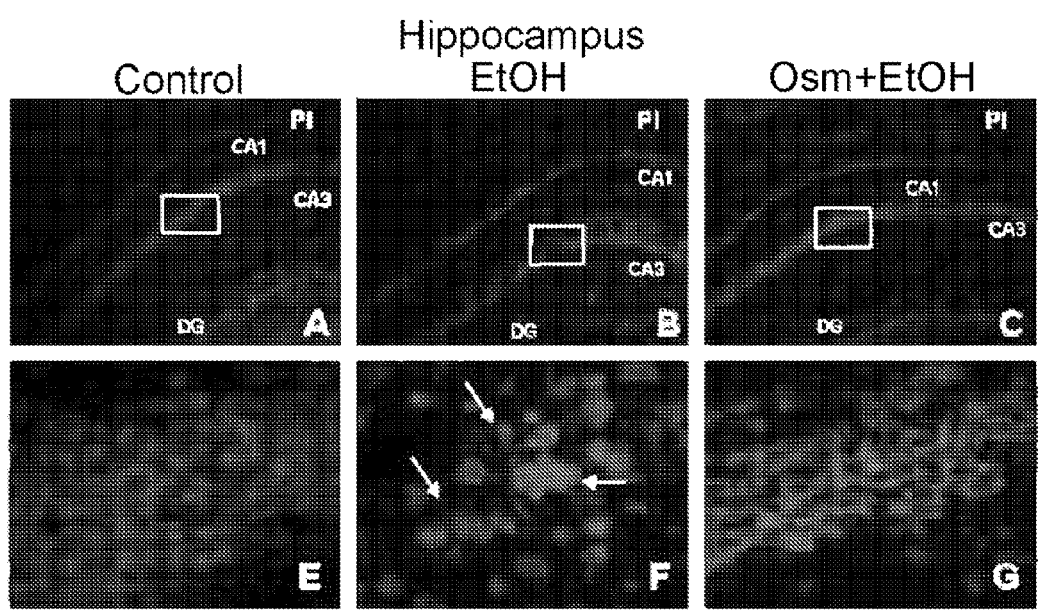
FIG. 6c shows the results of PI staining of the CA1, CA3 and DG areas of the brain hippocampus at postnatal day 7 (P 7) under exposure to ethanol, osmotin and osmotin plus ethanol.

In addition, in order to histologically examine ethanol-induced neurotoxicity in the hippocampus of the brains of developmental-stage rats, PI that indicates injured or dead neurons was used. The degree of injured or dead neurons in the control group, the ethanol-treated group and the ethanol plus osmotin-treated group was analyzed by visualizing fluorescence labeling (FIG. 6c). Ethanol induced severe neurodegeneration in the weak area of the brain, and this neurodegeneration corresponded to several times that of the control group. The number of PI-positive cells (shrunk or condensed nuclei and PI stained at high concentration) in the hippocampal CA1 significantly increased, suggesting that the number of PI-labeled injured cells in the ethanol-treated group was larger than that in the control group (FIGS. 6c, panels A-G). Unlike this, in the group treated with osmotin following ethanol treatment, the number of PI-positive cells in the weak brain area of developmental-stage rats significantly decreased.

INDUSTRIAL APPLICABILITY

The composition comprising osmotin according to the present invention can be used as a composition for preventing and treating neurological diseases and a health functional food composition.

What is claimed is:

1. A method for reducing alcohol-induced apoptosis in hippocampal and/or cortical neurons and/or for protecting hippocampal and/or cortical neurons from alcohol-induced cell damage the method comprising a step of administering a composition comprising osmotin to a subject, wherein the osmotin is a wild type osmotin from *Nicotiana tabacum, Citrus sinensis, Rosa roxburghii, Solanum tuberosum, Piper colubrinum, Ricinus communis,* or *Arabidopsis thaliana.*

2. The method of claim 1, wherein the method is achieved by inhibition of cytochrome-c release, a decrease in caspase expression, an increase in the Bcl-2/Bax ratio, and/or a decrease in $Ca^{2+}$ concentration in the hippocampal and/or cortical neurons.

3. The method of claim 2, wherein the composition is administered to the subject at a dose of osmotin from 0.1 µg/g to 500 µg/g.

4. The method of claim 2, wherein the method comprises reducing alcohol-induced apoptosis in at least one of hippocampal and cortical neurons.

5. The method of claim 2, wherein the method comprises protecting at least one of hippocampal and cortical neurons from alcohol-induced cell damage.

* * * * *